US008679067B2

(12) United States Patent  (10) Patent No.: US 8,679,067 B2
Wright  (45) Date of Patent: *Mar. 25, 2014

(54) MEDICAL TUBING SECUREMENT ASSEMBLY AND METHODS OF USE

(75) Inventor: Clifford A. Wright, San Diego, CA (US)

(73) Assignee: Venetec International, Inc., Covington, GA (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/470,719

(22) Filed: May 14, 2012

(65) Prior Publication Data

US 2012/0316505 A1  Dec. 13, 2012

Related U.S. Application Data

(63) Continuation of application No. 13/198,030, filed on Aug. 4, 2011, now Pat. No. 8,177,756, which is a continuation of application No. 11/532,194, filed on Sep. 15, 2006, now Pat. No. 8,052,649.

(60) Provisional application No. 60/718,619, filed on Sep. 19, 2005, provisional application No. 60/758,359, filed on Jan. 12, 2006.

(51) Int. Cl.
*A61M 5/32* (2006.01)

(52) U.S. Cl.
USPC ........................................ 604/174; 604/180

(58) Field of Classification Search
USPC ........................................ 604/174–180, 250
See application file for complete search history.

(56) References Cited

U.S. PATENT DOCUMENTS

| 2,402,306 A | 6/1946 | Turkel |
| 2,525,398 A | 10/1950 | Collins |
| 2,533,961 A | 12/1950 | Rousseau et al. |
| 2,707,953 A | 5/1955 | Ryan |
| 2,893,671 A | 7/1959 | Flora et al. |
| 3,059,645 A | 10/1962 | Hasbrouck |
| 3,064,648 A | 11/1962 | Bujan |
| 3,167,072 A | 1/1965 | Stone et al. |

(Continued)

FOREIGN PATENT DOCUMENTS

| EP | 0 114 677 A3 | 8/1984 |
| EP | 0 247 590 A2 | 12/1987 |

(Continued)

OTHER PUBLICATIONS

Cravens, et al., Urinary Catheter Management, American Family Physician, vol. 61, No. 2, pp. MDG 000273-MDG 000282, Jan. 15, 2000.

(Continued)

*Primary Examiner* — Theodore Stigell
(74) *Attorney, Agent, or Firm* — Knobbe Martens Olson & Bear LLP

(57) ABSTRACT

A medical tubing securement assembly includes a base having a disc, and a retaining adapter removably and rotatably attached to the disc. The retaining adapter includes a longitudinal passage for receiving a locking adapter. The locking adapter includes a longitudinal passage for receiving a medical tube. Once the tube is inserted into the locking adapter, the locking adapter may be rotated within the retaining adapter, around the tube, to secure the tube within the securement assembly.

20 Claims, 5 Drawing Sheets

(56) References Cited

U.S. PATENT DOCUMENTS

| | | |
|---|---|---|
| 3,245,567 A | 4/1966 | Knight |
| 3,394,954 A | 7/1968 | Sarns |
| 3,482,569 A | 12/1969 | Raffaelli, Sr. |
| 3,529,597 A | 9/1970 | Fuzak |
| 3,589,361 A | 6/1971 | Loper et al. |
| 3,602,227 A | 8/1971 | Andrew |
| 3,630,195 A | 12/1971 | Santomieri |
| 3,632,071 A | 1/1972 | Cameron et al. |
| 3,677,250 A | 7/1972 | Thomas |
| 3,686,896 A | 8/1972 | Rutter |
| 3,731,684 A | 5/1973 | Spiegel |
| 3,766,915 A | 10/1973 | Rychlik |
| 3,812,851 A | 5/1974 | Rodriguez |
| 3,834,380 A | 9/1974 | Boyd |
| 3,847,370 A | 11/1974 | Engelsher |
| 3,856,020 A | 12/1974 | Kovac |
| 3,863,631 A | 2/1975 | Baldwin |
| 3,896,527 A | 7/1975 | Miller et al. |
| 3,900,026 A | 8/1975 | Wagner |
| 3,901,226 A | 8/1975 | Scardenzan |
| 3,906,946 A | 9/1975 | Nordstrom |
| 3,920,001 A | 11/1975 | Edwards |
| 3,942,228 A | 3/1976 | Buckman et al. |
| 3,973,565 A | 8/1976 | Steer |
| 3,993,081 A | 11/1976 | Cussell |
| 4,004,586 A | 1/1977 | Christensen et al. |
| D243,477 S | 2/1977 | Cutruzzula et al. |
| 4,020,835 A | 5/1977 | Nordstrom et al. |
| 4,030,540 A | 6/1977 | Roma |
| 4,037,599 A | 7/1977 | Raulerson |
| 4,057,066 A | 11/1977 | Taylor |
| 4,059,105 A | 11/1977 | Cutruzzula et al. |
| 4,079,738 A | 3/1978 | Dunn et al. |
| 4,082,094 A | 4/1978 | Dailey |
| 4,114,618 A | 9/1978 | Vargas |
| 4,116,196 A | 9/1978 | Kaplan et al. |
| 4,123,091 A | 10/1978 | Cosentino et al. |
| 4,129,128 A | 12/1978 | McFarlane |
| 4,133,307 A | 1/1979 | Ness |
| 4,133,312 A | 1/1979 | Burd |
| 4,142,527 A | 3/1979 | Garcia |
| 4,149,539 A | 4/1979 | Cianci |
| 4,161,177 A | 7/1979 | Fuchs |
| 4,170,993 A | 10/1979 | Alvarez |
| 4,170,995 A | 10/1979 | Levine et al. |
| 4,193,174 A | 3/1980 | Stephens |
| 4,194,504 A | 3/1980 | Harms et al. |
| D256,162 S | 7/1980 | Haerr et al. |
| 4,224,937 A | 9/1980 | Gordon |
| 4,230,109 A | 10/1980 | Geiss |
| 4,248,229 A | 2/1981 | Miller |
| 4,250,880 A | 2/1981 | Gordon |
| 4,275,721 A | 6/1981 | Olson |
| 4,314,568 A | 2/1982 | Loving |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,362,156 A | 12/1982 | Feller, Jr. et al. |
| 4,392,853 A | 7/1983 | Muto |
| 4,397,647 A | 8/1983 | Gordon |
| 4,398,757 A | 8/1983 | Floyd et al. |
| 4,405,163 A | 9/1983 | Voges et al. |
| 4,405,312 A | 9/1983 | Gross et al. |
| 4,435,174 A | 3/1984 | Redmond et al. |
| 4,435,175 A | 3/1984 | Friden |
| 4,439,193 A | 3/1984 | Larkin |
| 4,442,994 A | 4/1984 | Logsdon |
| D273,993 S | 5/1984 | Schulte et al. |
| 4,449,975 A | 5/1984 | Perry |
| 4,453,933 A | 6/1984 | Speaker |
| 4,470,410 A | 9/1984 | Elliott |
| 4,474,559 A | 10/1984 | Steiger |
| 4,480,639 A | 11/1984 | Peterson et al. |
| 4,484,913 A | 11/1984 | Swauger |
| 4,516,968 A | 5/1985 | Marshall et al. |
| 4,517,971 A | 5/1985 | Sorbonne |
| 4,561,857 A | 12/1985 | Sacks |
| 4,563,177 A | 1/1986 | Kamen |
| 4,579,120 A | 4/1986 | MacGregor |
| 4,583,976 A | 4/1986 | Ferguson |
| 4,585,435 A | 4/1986 | Vaillancourt |
| 4,585,444 A | 4/1986 | Harris |
| 4,631,056 A | 12/1986 | Dye |
| 4,633,863 A | 1/1987 | Filips et al. |
| 4,650,473 A | 3/1987 | Bartholomew et al. |
| 4,659,329 A | 4/1987 | Annis |
| 4,660,555 A | 4/1987 | Payton |
| 4,666,434 A | 5/1987 | Kaufman |
| 4,693,710 A | 9/1987 | McCool |
| 4,711,636 A | 12/1987 | Bierman |
| 4,723,948 A | 2/1988 | Clark et al. |
| 4,726,716 A | 2/1988 | McGuire |
| 4,737,143 A | 4/1988 | Russell |
| 4,742,824 A | 5/1988 | Payton et al. |
| 4,743,231 A | 5/1988 | Kay et al. |
| 4,752,292 A | 6/1988 | Lopez et al. |
| 4,762,513 A | 8/1988 | Choy et al. |
| 4,792,163 A | 12/1988 | Kulle |
| 4,795,429 A | 1/1989 | Feldstein |
| 4,808,162 A | 2/1989 | Oliver |
| 4,823,789 A | 4/1989 | Beisang, III |
| 4,826,486 A | 5/1989 | Palsrok et al. |
| 4,834,702 A | 5/1989 | Rocco |
| 4,834,716 A | 5/1989 | Ogle, II |
| 4,838,858 A | 6/1989 | Wortham et al. |
| 4,838,878 A | 6/1989 | Kalt et al. |
| D302,304 S | 7/1989 | Kulle et al. |
| 4,846,807 A | 7/1989 | Safadago |
| 4,852,844 A | 8/1989 | Villaveces |
| 4,857,058 A | 8/1989 | Payton |
| 4,863,432 A | 9/1989 | Kvalo |
| 4,869,465 A | 9/1989 | Yirmiyahu et al. |
| 4,878,897 A | 11/1989 | Katzin |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,899,963 A | 2/1990 | Murphy |
| 4,919,654 A | 4/1990 | Kalt |
| 4,932,943 A | 6/1990 | Nowak |
| 4,934,375 A | 6/1990 | Cole et al. |
| 4,941,882 A | 7/1990 | Ward et al. |
| 4,944,728 A | 7/1990 | Carrell et al. |
| 4,952,207 A | 8/1990 | Lemieux |
| 4,955,864 A | 9/1990 | Hajduch |
| 4,966,582 A | 10/1990 | Sit et al. |
| 4,976,700 A | 12/1990 | Tollini |
| 4,981,469 A | 1/1991 | Whitehouse et al. |
| 4,997,421 A | 3/1991 | Palsrok et al. |
| 5,000,741 A | 3/1991 | Kalt |
| 5,024,665 A | 6/1991 | Kaufman |
| 5,037,397 A | 8/1991 | Kalt et al. |
| 5,037,398 A | 8/1991 | Buchanan |
| 5,037,405 A | 8/1991 | Crosby |
| 5,073,166 A | 12/1991 | Parks et al. |
| 5,073,170 A | 12/1991 | Schneider |
| D323,390 S | 1/1992 | Paine et al. |
| 5,084,026 A | 1/1992 | Shapiro |
| 5,098,048 A | 3/1992 | Chen |
| 5,098,399 A | 3/1992 | Tollini |
| 5,100,393 A | 3/1992 | Johnson |
| 5,105,807 A | 4/1992 | Kahn et al. |
| 5,112,313 A | 5/1992 | Sallee |
| 5,135,506 A | 8/1992 | Gentelia et al. |
| 5,137,519 A | 8/1992 | Littrell et al. |
| 5,147,322 A | 9/1992 | Bowen et al. |
| 5,156,641 A | 10/1992 | White |
| 5,188,609 A | 2/1993 | Bayless et al. |
| 5,192,273 A | 3/1993 | Bierman et al. |
| 5,192,274 A | 3/1993 | Bierman |
| 5,195,981 A | 3/1993 | Johnson |
| 5,226,892 A | 7/1993 | Boswell |
| 5,234,185 A | 8/1993 | Hoffman et al. |

(56) References Cited

U.S. PATENT DOCUMENTS

| | | |
|---|---|---|
| 5,248,306 A | 9/1993 | Clark et al. |
| 5,250,041 A | 10/1993 | Folden et al. |
| 5,263,943 A | 11/1993 | Vanderbrook |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,314,411 A | 5/1994 | Bierman |
| 5,322,514 A | 6/1994 | Steube et al. |
| 5,330,438 A | 7/1994 | Gollobin et al. |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,368,575 A | 11/1994 | Chang |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |
| 5,395,344 A | 3/1995 | Beisang, III et al. |
| 5,398,679 A | 3/1995 | Freed |
| 5,403,285 A | 4/1995 | Roberts |
| 5,413,562 A | 5/1995 | Swauger |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,484,425 A | 1/1996 | Fischell et al. |
| 5,496,282 A | 3/1996 | Militzer et al. |
| 5,496,283 A | 3/1996 | Alexander |
| 5,499,976 A | 3/1996 | Dalton |
| 5,507,535 A | 4/1996 | McKamey et al. |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,626,565 A | 5/1997 | Landis et al. |
| 5,632,274 A | 5/1997 | Quedens et al. |
| 5,643,217 A | 7/1997 | Dobkin |
| 5,672,159 A | 9/1997 | Warrick |
| 5,681,290 A | 10/1997 | Alexander |
| 5,685,859 A | 11/1997 | Kornerup |
| 5,690,617 A | 11/1997 | Wright |
| 5,697,907 A | 12/1997 | Gaba |
| 5,738,660 A | 4/1998 | Luther |
| 5,755,225 A | 5/1998 | Hutson |
| 5,795,335 A | 8/1998 | Zinreich |
| 5,885,251 A | 3/1999 | Luther |
| 5,944,696 A | 8/1999 | Bayless et al. |
| 6,001,081 A | 12/1999 | Collen |
| 6,027,480 A | 2/2000 | Davis et al. |
| 6,074,368 A | 6/2000 | Wright |
| 6,113,577 A | 9/2000 | Hakky et al. |
| 6,132,398 A | 10/2000 | Bierman |
| D433,503 S | 11/2000 | Powers et al. |
| 6,213,979 B1 | 4/2001 | Bierman |
| 6,213,996 B1 | 4/2001 | Jepson et al. |
| 6,228,064 B1 | 5/2001 | Abita et al. |
| 6,231,548 B1 | 5/2001 | Bassett |
| 6,283,945 B1 | 9/2001 | Bierman |
| 6,290,676 B1 | 9/2001 | Bierman |
| 6,332,874 B1 | 12/2001 | Eliasen et al. |
| 6,361,523 B1 | 3/2002 | Bierman |
| 6,413,240 B1 | 7/2002 | Bierman et al. |
| 6,428,514 B1 | 8/2002 | Goebel et al. |
| 6,447,485 B2 | 9/2002 | Bierman |
| 6,458,104 B2 | 10/2002 | Gautsche |
| 6,500,154 B1 | 12/2002 | Hakky et al. |
| 6,585,703 B1 | 7/2003 | Kassel et al. |
| 6,663,600 B2 | 12/2003 | Bierman et al. |
| 6,786,892 B2 | 9/2004 | Bierman |
| 6,827,705 B2 | 12/2004 | Bierman |
| 6,837,875 B1 | 1/2005 | Bierman |
| 6,872,194 B2 | 3/2005 | Doyle et al. |
| 6,929,625 B2 | 8/2005 | Bierman |
| 6,951,550 B2 | 10/2005 | Bierman |
| 6,984,145 B1 | 1/2006 | Lim et al. |
| 7,018,362 B2 | 3/2006 | Bierman et al. |
| 7,247,150 B2 | 7/2007 | Bierman |
| 8,052,649 B2 * | 11/2011 | Wright .......... 604/174 |
| 8,177,756 B2 * | 5/2012 | Wright .......... 604/174 |
| 2005/0192539 A1 | 9/2005 | Bierman et al. |
| 2006/0129103 A1 | 6/2006 | Bierman et al. |
| 2006/0233652 A1 | 10/2006 | Kim et al. |
| 2007/0142782 A2 | 6/2007 | Bierman |
| 2007/0276335 A1 | 11/2007 | Bierman |

FOREIGN PATENT DOCUMENTS

| | | |
|---|---|---|
| EP | 0 263 789 A1 | 4/1988 |
| EP | 0 356 683 A1 | 3/1990 |
| EP | 0 367 549 A3 | 5/1990 |
| EP | 0 720 836 | 7/1996 |
| EP | 0 931 560 | 7/1999 |
| FR | 1 184 139 A | 7/1959 |
| FR | 2 381 529 | 9/1978 |
| FR | 2 598 625 A | 11/1987 |
| GB | 2 063 679 | 6/1981 |
| GB | 2 086 466 | 5/1982 |
| GB | 2 178 811 | 2/1987 |
| GB | 2210934 A | 11/1989 |
| GB | 2 288 542 A | 10/1995 |
| JP | 04-51767 | 6/1905 |
| JP | 07-28563 | 6/1905 |
| JP | 60-051377 | 3/1985 |
| JP | 04-037448 | 2/1992 |
| JP | 06-344852 | 12/1994 |
| JP | 08-257138 | 10/1996 |
| NL | 1015663 | 1/2002 |
| WO | WO 80/01458 | 7/1980 |
| WO | WO 85/02774 | 7/1985 |
| WO | WO 90/05559 | 5/1990 |
| WO | WO 91/16939 | 11/1991 |
| WO | WO 92/19309 | 11/1992 |
| WO | WO 92/19314 | 11/1992 |
| WO | WO 96/10435 | 4/1996 |
| WO | WO 96/26756 | 9/1996 |
| WO | WO 97/15342 | 5/1997 |
| WO | WO 98/53872 | 12/1998 |

OTHER PUBLICATIONS

Dale® Foley Catheter Holder brochure, pp. MDG 000344-MDG 000346, 2002.

European Search Report for Application No. EP 04 07 7158.6 dated Feb. 14, 2005.

European Search Report for application No. EP 04 07 6329, 3 pp., Feb. 7, 2005.

European Search Report for EP 06 11 4046 dated Feb. 12, 2007.

Expert Discusses Strategies to Prevent CAUTIs, Infection Control Today, pp. MDG 000603-MDG-000609, Jun. 2005.

Grip-Lok Universal Tubing Securement brochure, pp. MDG 000364-MDG 000366, 2005-2006.

Multiple-Lumen Central Venous Catheterization Product with ARROW+gard™ Antiseptic Surface (Arrow International brochure) (Apr. 1994).

(56) References Cited

OTHER PUBLICATIONS

National Patent Services, Search Report re Patent Validity Study of U.S. Patent 5827230, pp. MDG 001319-MDG 001320, May 23, 2006.

Extended European Search Report for EP Application No. 06803762.1, dated Jun. 24, 2011 in 6 pages.

United States Patent and Trademark Office, Combined Search Report and Written Opinion for PCT/US2006/036235, dated Apr. 25, 2007.

* cited by examiner

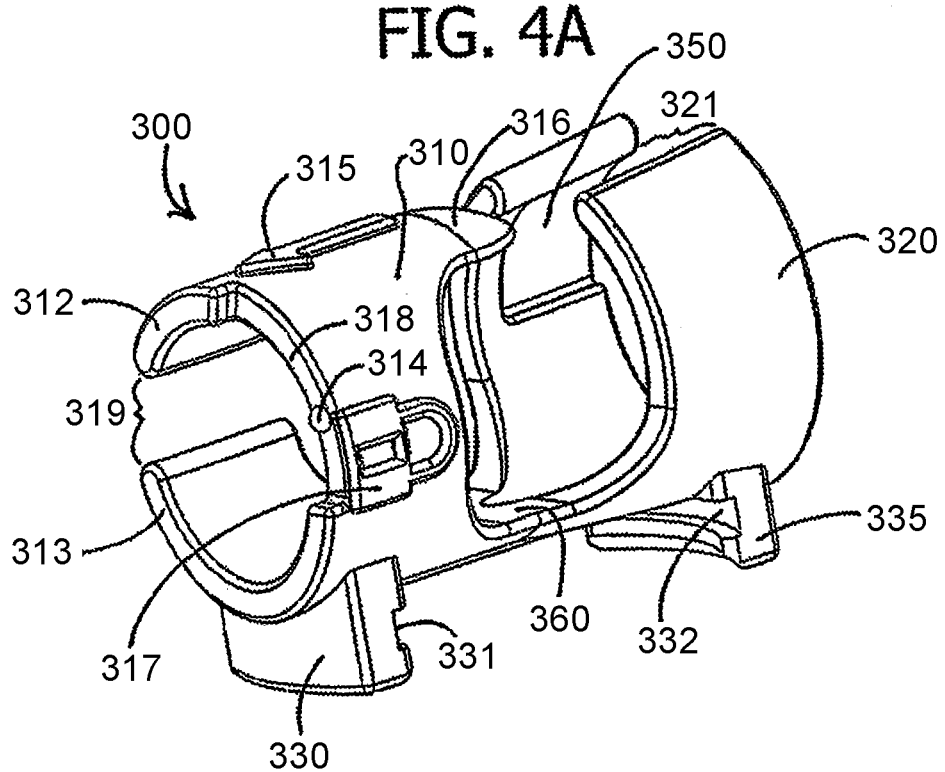
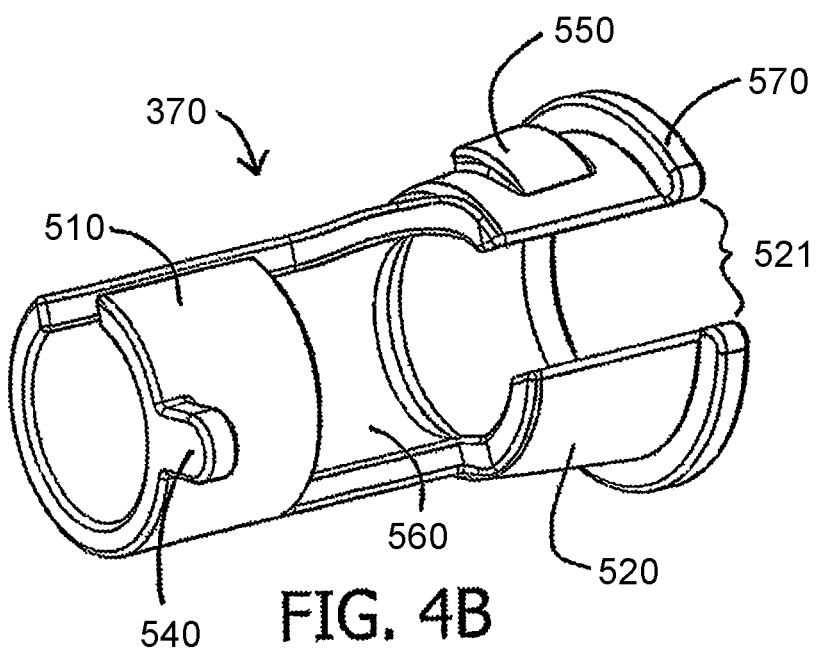

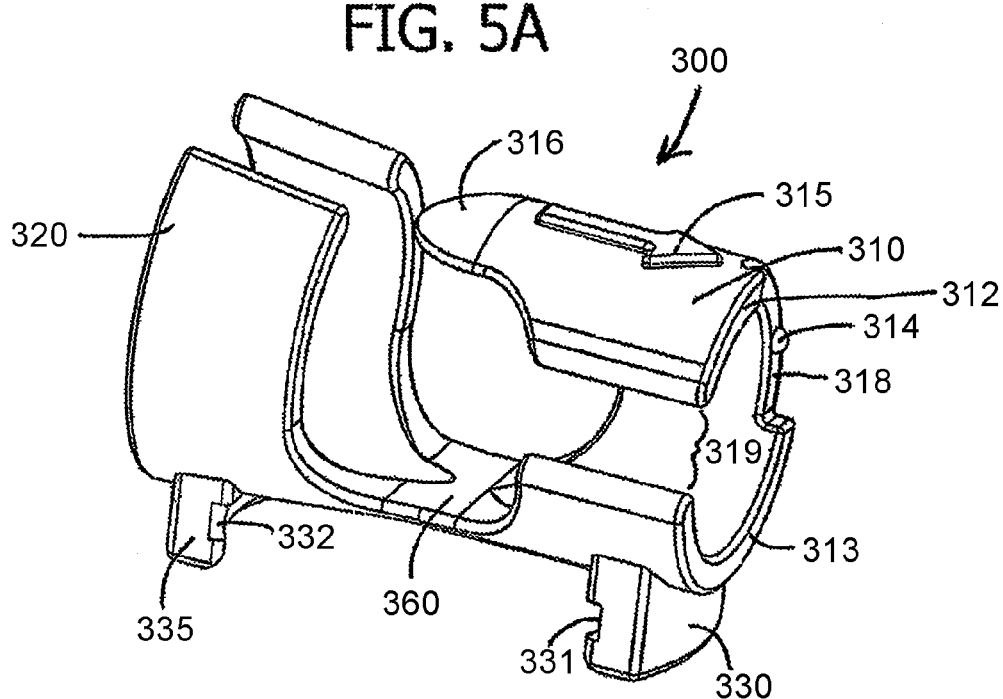
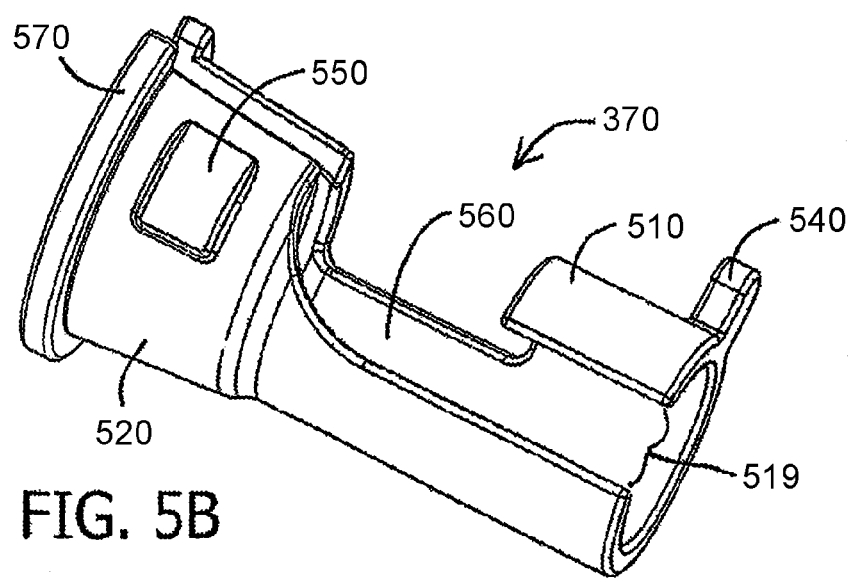

MEDICAL TUBING SECUREMENT ASSEMBLY AND METHODS OF USE

CROSS-REFERENCE TO RELATED APPLICATIONS

This application is a continuation of U.S. patent application Ser. No. 13/198,030, filed Aug. 4, 2011, entitled MEDICAL TUBING SECUREMENT ASSEMBLY AND METHODS OF USE, now U.S. Pat. No. 8,177,756, which is a continuation of U.S. patent application Ser. No. 11/532,194, filed Sep. 15, 2006, now U.S. Pat. No. 8,052,649, entitled MEDICAL TUBING SECUREMENT ASSEMBLY AND METHODS OF USE, which claims priority under 35 U.S.C. §119(e) to U.S. Provisional Patent Application No. 60/718,619, filed Sep. 19, 2005, and U.S. Provisional Patent Application No. 60/758,359, filed Jan. 12, 2006, each of which is hereby incorporated by reference in its entirety.

TECHNICAL FIELD

The present invention relates in general to a device for securing medical tubing, such as a Foley catheter, to a patient.

BACKGROUND

The use of medical tubing in various surgical and therapeutic treatments or during recovery is well known in the art. For example, urinary catheters, CVCs, hemodialysis catheters, suprapubic catheters, surgical drainage tubes, feeding tubes, chest tubes, nasogastric tubes, scopes, as well as electrical wires or cables connected to external or implanted electronic devices or sensors, are some of the various types of medical tubing that are employed by medical practitioners. With respect to urinary catheters, some of the more common types include Foley catheters, Coudé catheters, and Pezzer or mushroom catheters. With respect to urological procedures, catheterization often involves inserting a tube (urinary catheter) through the urethra into the bladder to remove urine. The bladder is sterile, so surgical asepsis must be used when performing this procedure. A urinary catheter is generally indicated when a person is unable to void naturally due to injury or a disease process, has had abdominal surgery, or is voiding overflow.

There are many different types of urinary catheters and each has a particular purpose. A Coudé catheter has a tapered tip that is designed for easy insertion when enlargement of the prostate is suspected. A Foley catheter has a balloon in its tip that is inflated after insertion so that it remains in the bladder. A Pezzer or Mushroom catheter has a triangular or knot-like tip and is used to drain urine from the renal pelvis; it can also be used for a suprapubic catheterization.

Simple urethral catheters are designed for in-and-out procedures. A three-way indwelling catheter has a balloon in its tip that is inflated after it is inserted and also has another tube or lumen that can be used for continuous bladder irrigation. A suprapubic catheter is surgically inserted through the abdominal wall above the symphysis and into the bladder to divert urine from the urethra.

Foley catheters typically include a soft, thin rubber tube with a balloon on one end. The catheter is threaded through the urinary duct (urethra) and into the bladder to drain urine from the bladder. A Foley catheter is typically used when normal urination is disrupted by an infection, a swollen prostate gland, bladder stones, or, sometimes, an injury. In very sick people, a catheter may be used to keep track of urine production.

A typical Foley catheter has a drainage lumen and an inflation lumen for inflating and deflating the balloon. The balloon is normally deflated until properly positioned in a patient's bladder by inserting the catheter through the urinary tract of the patient and advancing the catheter until the tip of the catheter reaches the patient's bladder. Although the catheter usually includes a siliconized outer coating, as provided by the manufacturer, healthcare providers often apply further lubricant, such as a water-based jelly. Once the catheter is properly positioned, the inflation lumen delivers fluid (e.g., saline solution) to inflate the balloon. Once-inflated, a valve, which is located at the inflation port, inhibits the flow of fluid from the inflation lumen and the balloon to keep the balloon inflated. The inflated balloon prevents the catheter from unintentionally dislodging from the bladder. The healthcare provider then connects the distal end of the drainage lumen (i.e., its effluent port) to a drainage tube leading to a collection container.

Once a Foley catheter, or other tubing, is inserted into, the patient, the part of the tubing that is on the outside of the patient (extracorporeal tubing) is typically secured to the patient's body using medical tape. This is done to reduce the risk of accidentally pulling or dislodging the tubing by inadvertently wrapping it around a limb or bedrail or knocking it out of position. With respect to Foley catheters, the healthcare provider commonly places long pieces of tape across the distal end of the catheter in a crisscross pattern to secure the catheter distal end to the inner thigh of the patient.

Medical tape has proven to be an unsatisfactory and crude means of securing medical tubing to a patient. One problem is that medical tape can crush the tubing and impede fluid flow. Another problem is that medical tape does not provide any freedom of movement to the tubing with respect to the patient's body. Consequently, any movement in the tubing caused by the patient's movements may cause the tape to twist and peel away from the skin and to generally fail. Yet another problem is that medical tape often collects contaminants and dirt. Standard protocol therefore typically requires periodic tape changes in order to inhibit bacteria and germ growth at the securement site.

Frequent tape changes may, however, lead to another problem: excoriation of the patient's skin. In addition, valuable healthcare provider time is spent applying and reapplying the tape to secure the catheter. And healthcare providers often remove their gloves when taping because most find the taping procedure difficult and cumbersome when wearing gloves. Not only does this further lengthen the procedure, but it also subjects the healthcare provider to possible infection.

Thus, it is highly desirable to have a new and improved device and method for securing medical tubing to a patient that overcomes the problems associated with medical tape.

SUMMARY

A medical tubing securement assembly includes a base having a disc, and a retaining adapter removably and rotatably attached to the disc. The retaining adapter includes a longitudinal passage for receiving a locking adapter. The locking adapter includes a longitudinal passage for receiving a medical tube. Once the tube is inserted into the locking adapter, the locking adapter may be rotated within the retaining adapter, around the tube, to secure the tube within the securement assembly.

Other features and advantages of the invention will appear hereinafter. The features of the invention described above can be used separately or together, or in various combinations of one or more of them. The invention resides as well in subcombinations of the features described. Furthermore, many of the method steps described herein may be performed in a different order than that which is explicitly described.

BRIEF DESCRIPTION OF THE DRAWINGS

In the drawings, wherein the same reference number indicates the same element throughout the several views:

FIGS. 4A and 5A are alternate perspective views of the retaining adapter of the medical tubing securement assembly depicted in FIG. 1.

FIGS. 4B and 5B are alternate perspective views of the locking adapter of the medical tubing securement assembly depicted in FIG. 1.

DETAILED DESCRIPTION

Various embodiments of the invention will now be described. The following description provides specific details for a thorough understanding and enabling description of these embodiments. One skilled in the art will understand, however, that the invention may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments of the invention. Certain terms may even be emphasized below; however, any terminology intended to be interpreted in any restricted manner will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

For ease of description, the present embodiments of the medical tubing securement assembly will be described in the context of securing an exemplary Foley catheter. The principles of the present invention, however, are not limited to Foley catheters. Indeed, it will be understood by one of skill in the art, in view of the present disclosure, that the medical tubing securement assembly disclosed herein can also be used to secure other types of medical tubing, including tubes for fluid communication and electrical wires.

The medical tubing securement assemblies disclosed herein may be adapted to retain other types of urinary catheters, including, but not limited to, CVCs, hemodialysis catheters, suprapubic catheters, surgical drainage tubes, feeding tubes, chest tubes, nasogastric tubes, scopes, as well as electrical wires or cables connected to external or implanted electronic devices or sensors. One skilled in the art may also find additional applications for the devices disclosed herein. Thus, the illustrations and descriptions of securement assemblies disclosed herein in connection with a Foley catheter are merely exemplary of one possible application of the device.

Figure 1:
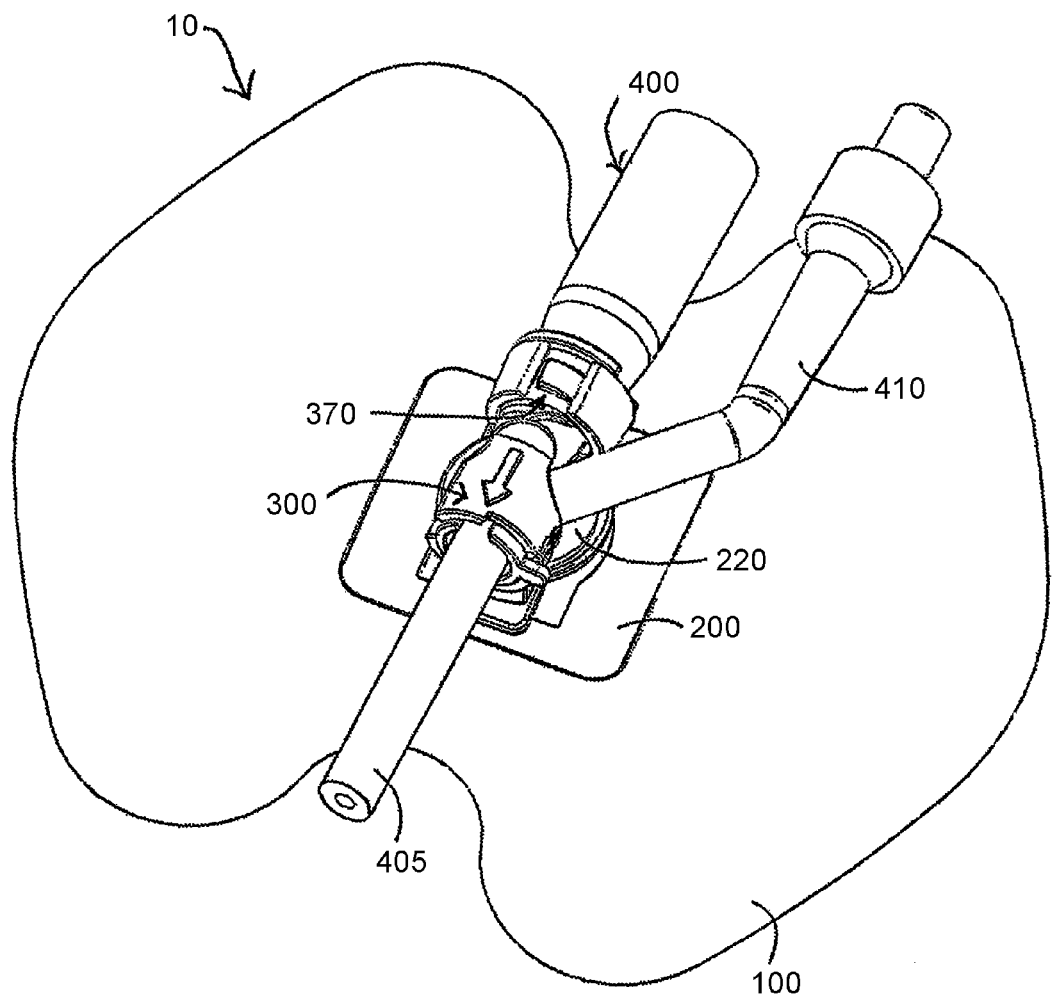
FIG. 1 is a perspective view of a medical tubing securement assembly securing a Foley catheter.

Referring now to the drawings, FIG. 1 illustrates a medical tubing securement assembly 10 in which an exemplary Foley catheter 400 is secured. The Foley catheter 400 includes a primary tube 405 and a secondary tube or inflation lumen 410. The medical tubing securement assembly 10 secures the Foley catheter 400 firmly in place against a patient's skin, via a base pad 100. In the case of the Foley catheter 400, the base pad 100 may be secured to the patient's thigh.

Figure 2:
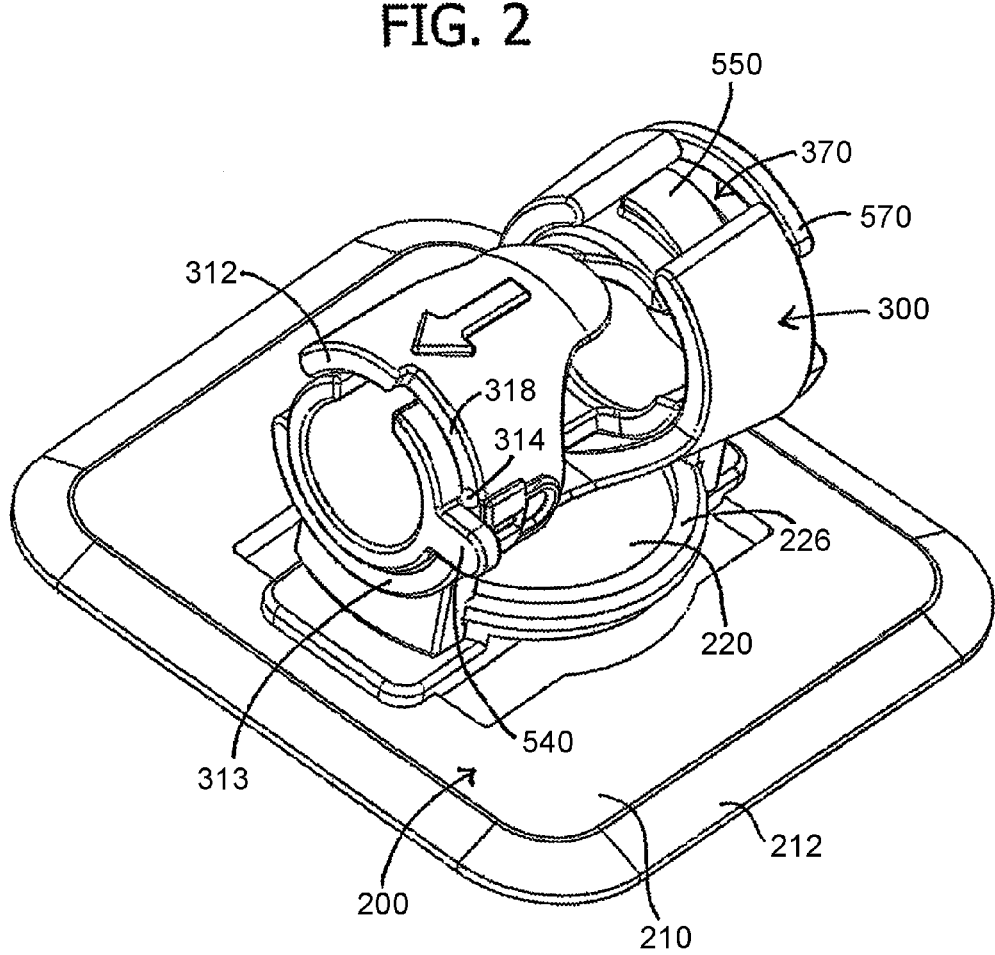
FIG. 2 is a perspective view of the medical tubing securement assembly depicted in FIG. 1 with the base pad and the Foley catheter removed.

As illustrated in FIGS. 1 and 2, the securement assembly 10 includes the base pad 100, a base plate 200, a retaining adapter 300, and a locking adapter 370 or catheter fitting mount. The retaining adapter 300 is preferably rotatable about a disc 220 on the base plate 200. Alternatively, the retaining adapter 300 may be fixedly secured to the disc 220, and the disc 220 may be rotatable about the base plate 200. Removable wax backing strips (not shown) are optionally included on a bottom surface of the base pad 100.

In one embodiment, the top surface of the base pad 100 may be secured to the bottom surface of the base plate 200 with a non-skin irritating adhesive. The bottom surface of the base plate 200 or the top surface of the base pad 100 may be coated with the non-skin irritating adhesive. The securement assembly 10 may then be secured to the patient's skin by removing the wax paper strips and adhering the bottom surface of the base pad 100 to the skin, or in any other suitable manner.

In another embodiment, as shown in FIG. 1, the bottom surface of the base pad 100 may be secured to the top surface of the base plate 200, along the edges of the base plate 200, with a non-skin irritating adhesive. The non-skin irritating adhesive may be coated on the bottom surface of the base pad 100 or on the edges of the top surface of the base plate 200. The base pad 100 can therefore sandwich the base plate 200 between the bottom surface of the base pad 100 and the patient's skin. In addition, the bottom surface of the base plate 200 can be coated with a non-skin irritating adhesive, and both the bottom surface of the base pad 100 and the bottom surface of the base plate 200 can be adhered to the skin of the patient.

Alternatively, the base plate 200 can be sandwiched between the base pad 100 and a layer of double-sided medical tape secured to the bottom surface of the base plate 200. The double-sided medical tape may be coated with a non-skin irritating adhesive to secure the top surface of the tape to the bottom surface of the base plate 200, and the bottom surface of the tape to the patient's skin.

Figure 3:
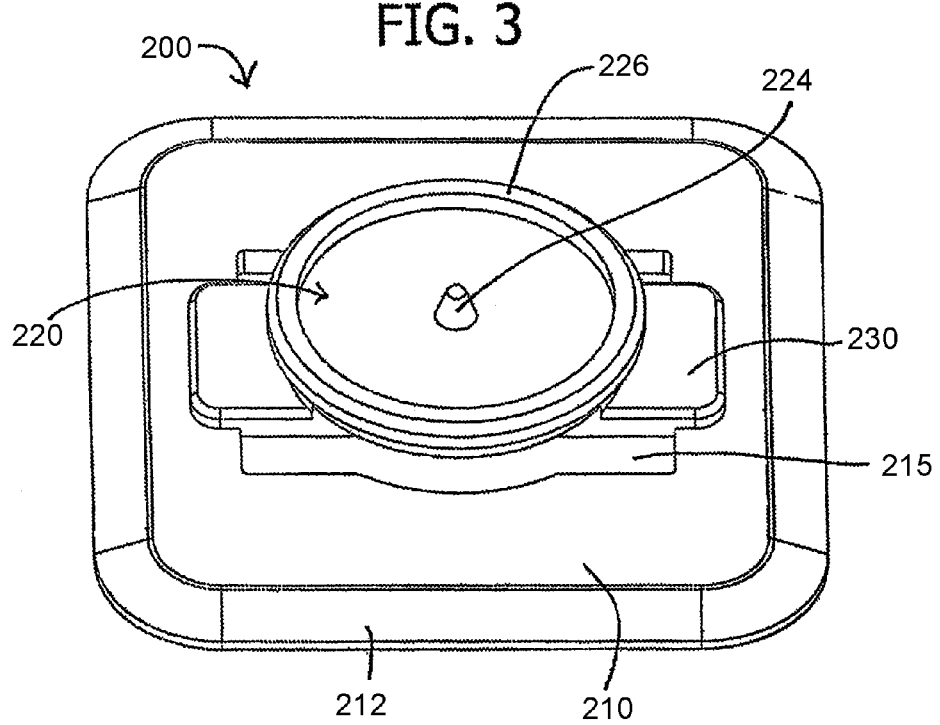
FIG. 3 is a perspective view of the base plate depicted in FIGS. 1 and 2.

Turning to FIG. 3, in one embodiment, the base plate 200 includes a platform 210 with a substantially flat top surface and a substantially flat bottom surface. The edges 212 of the platform 210 may optionally be sloped. The platform 210 may be shaped as a square, a rectangle, a circle, an oval, or may have any other suitable configuration. For example, the platform may include two opposing arms extending in a distal direction toward the patient's site of incision or catheter insertion, as opposed to having a uniform square shape, as described in U.S. Provisional Application Ser. No. 60/718,619 filed, Sep. 19, 2005, which is incorporated herein by reference.

The platform 210 optionally includes a central opening 215 over which a bridge 230 extends. The disc 220 rests atop the bridge 230. One or more raised pedestals (not shown) may optionally be included atop the platform to provide additional support to the retaining adapter 300 as it rotates atop the disc 220. The disc 220 may have any suitable diameter, preferably between 0.5 cm to 5.0 cm. In one embodiment, the disc has a diameter of approximately 1.8 cm. The disc 220 preferably has a substantially flat top surface and includes a protuberance 224 at its center, which forms a spindle. The protuberance 224 may be cone-shaped, round or hemispherical, bell-shaped, or have any other suitable configuration. A raised ring 226 optionally forms a lip or snap-ring at an outer rim of the disc 220. The retaining adapter 300 preferably snaps or otherwise fits onto the lip formed by the raised ring 226, as described below.

The platform 210, bridge 230, disc 220, protuberance 224, and ring 226 of the base plate 200 may optionally be a unibody construction made from a single mold. Alternatively, one or more of these components may be formed from one or more separate molds and connected to the other components via adhesive, welding, or via any other suitable manner. Each of the components of the medical securement assembly 10 may be made of any suitable material, such as a flexible plastic or elastomeric material.

Turning to FIGS. 4A and 5A, the retaining adapter 300 includes a proximal sleeve 320 forming an upper opening 321, a distal sleeve 310 forming a lateral opening 319, and a bridge 360 connecting the two. (As used herein, the proximal direction is from the center of the securement assembly 10 toward the proximal sleeve 320, and the distal direction is from the center of the securement assembly 10 toward the distal sleeve 310.) The upper opening 321 is preferably not in longitudinal alignment with the lateral opening 319. The upper opening 321 is preferably shifted by 1° to 120°, or 45° to 100°, or 60° to 90°, with respect to the lateral opening 319. In one embodiment, the upper opening 321 is shifted approximately 90° with respect to the lateral opening 319.

The distal edge of the distal sleeve 310 optionally forms a substantially backwards "C" shape. The distal edge preferably includes a recessed section 318 defined between a first raised section 312 and a second raised section 313. A protuberance or projection 314 preferably resides within the recessed section 318 for securing the locking adapter 370 into the locked position, as described below. The proximal sleeve 320 optionally includes a recessed section 350 or indentation on an inner surface thereof for accommodating a raised wedge 550 or elevated segment on the locking adapter 370, as described below.

The distal sleeve 310 may include one or more directional markers, such as an arrow 315 and a lock indicator 317. The arrow 315 preferably points in the distal direction toward the intended site of incision or insertion of the catheter. The lock indicator 317 indicates the position to which a lever 540 on the locking adapter 370 should be rotated to secure the Foley catheter 400 within the securement assembly 10, as described below. The distal sleeve 310 also preferably includes a retainer tab 316 that extends from the top side of the distal sleeve 310 toward the proximal sleeve 320. The distal sleeve 310 and the proximal sleeve 320 are preferably connected at their bottom portions via the bridge 360, leaving the remainder of the sleeves 310 and 320 disjoined.

Accordingly, a gap exists between the proximal sleeve 320 and the distal sleeve 310 that extends substantially perpendicularly to the longitudinal axis of the retaining adapter 300. The gap can accommodate, and provides a passageway for, a side branch of a medical tube, such as the inflation lumen 410 of the Foley catheter 400. The gap, in conjunction with the lateral opening 319, also provides an opening into which the Foley catheter may be inserted, as described below.

In one embodiment, the retaining adapter 300 is secured or attached to the base plate 200 in a manner allowing it to rotate or spin atop the disc 220. The retaining adapter 300 includes a front or distal support 330 with a first connection groove 331, and a rear or proximal support 335 with a second connection groove 332. The raised ring 226 on the disc 220 may be inserted into the first and second connection grooves 331 and 332 to provide a track on which the distal and proximal supports 330 and 335 slide or run. This connection between the retaining adapter 300 and the disc 220 allows the adapter 300 to rotate atop the disc 220. Alternatively, the retaining adapter 300 may be fixedly secured to the disc 220, and the disc 220 may be rotatable about the bridge 230 or the platform 210 of the base plate 200.

The retaining adapter 300 preferably includes a cavity or opening (not shown) on its bottom surface, approximately midway between the distal support 330 and the proximal support 335. The cavity mates with the protuberance 224 on the disc 220. The bottom surface of the retaining adapter 300 is preferably spaced apart from the top surface of the disc 220. The gap provided by this spacing reduces friction between the retaining adapter 300 and the disc 220 when the retaining adapter 300 is rotated, allowing for freer rotation of the retaining adapter 300 atop the disc 220.

The retaining adapter 300 is secured to the disc 220 via insertion of the raised ring 226 into the first and second connection grooves 331 and 332. Although the retaining adapter 300 is preferably removable, it cannot be removed from the disc 220 simply by pulling the retaining adapter 300 in an upward manner; the groove/ring connection prohibits such detachment. The retaining adapter 300, however, is preferably made of a flexible material that allows the bridge 360 of the retaining adapter 300 to flex or bend.

When the proximal and distal sleeves 320 and 310 of the retaining adapter 300 are squeezed toward each other, the bridge 360 flexes such that the proximal and distal sleeves 320 and 310 tilt inwardly toward each other, and the proximal and distal supports 335 and 330 are forced upward and away from each other. This upward and outward movement of the proximal and distal supports 335 and 330 frees the ring 226 from the proximal and distal connection grooves 332 and 331, consequently freeing the retaining adapter 300 from the disc 220. Thus, the retaining adapter 300 can be detached from the disc 220 by squeezing the proximal and distal sleeves 320 and 310 toward each other. The adapter 300 can be reattached to the disc 220 by positioning one of the connection grooves 331 and 332 over the ring 226 and snapping or otherwise forcing the other connection groove over the ring 226. The bend able bridge 360 returns to its original substantially level state unless a force causes it to bend out of its level state.

In one embodiment, as shown in FIGS. 1-3, the disc 220 is oriented horizontally or parallel to the platform 210 of the base plate 200. In another embodiment (not shown), the disc 220 is attached at an angle in relation to the platform 210. For example, the disc 220 may be at an angle of approximately 1° to 30° in relation to the platform 210. In one embodiment, the disc 220 is at an angle of approximately 5°, or 10°, or 15°, or 20°, or 25°, or 30°, in relation to the platform 210. This angle of inclination may be accomplished by raising one side of the bridge 230 relative to the other side of the bridge 230. A side of the bridge 230 can be raised by adding a step underneath that side of the bridge 230, or by making one side of the bridge 230 thicker than the other side, or in any other suitable manner. This angled configuration may be used to provide, for example, an angle of inclination for directing the medical tubing toward the patient's skin.

Turning to FIGS. 48 and 58, the locking adapter 370 includes a proximal sleeve 520 forming a first opening 521, a distal sleeve 510 forming a second opening 519, and a substantially arcuate or semi-circular bridge 560 connecting the two. The distal sleeve 510 includes a lever 540 or handle for facilitating manual rotation of the locking adapter 370, when the locking adapter 370 is positioned within the retaining adapter 300, as described below.

The proximal sleeve 520 optionally includes a wedge 550 or other elevated segment on an outer surface thereof for providing an interference fit with an inner surface of the proximal sleeve 320 of the retaining adapter 300 (as is best shown in FIG. 2). The wedge 550 is preferably dimensioned to fit within the recessed section 350 in the inner surface of the proximal sleeve 320 of the retaining adapter 300 when the locking adapter 370 is in an unlocked position, such that little or no interference fit occurs in the unlocked position.

The proximal sleeve 520 further preferably includes a raised outer rim 570 or edge that abuts a proximally outer surface of the proximal sleeve 320, as shown in FIG. 2, to substantially limit or prevent distal movement of the locking adapter 370 within the retaining adapter 300. The outer dimensions of the distal and proximal sleeves 510 and 520 of the locking adapter 370 are preferably substantially complementary with the inner dimensions of the distal and proximal sleeves 310 and 320 of the retaining adapter 300 so that the locking adapter 370 fits closely within, and is rotatable within, the retaining adapter 300, as described below.

The opening 519 in the distal sleeve 510 is preferably wide enough to accommodate a medical tube, such as the Foley catheter 40, when the tube is squeezed through the opening 519 and into the space or tunnel formed by the inner surface of the distal sleeve 510. Alternatively, the opening 519 may be narrower than the medical tube, as long as the locking adapter 370 (and the retaining adapter 300) is made of a material flexible enough to allow the opening 519 to be enlarged by pushing the free opposing surfaces of the distal sleeve 510 away from each other to allow the medical tube to be squeezed through the opening 519. Once the medical tube is squeezed through the opening 519 the distal sleeve 510 returns to its original shape.

Similarly, the opening 521 in the proximal sleeve 520 is preferably wide enough that a medical tube, such as the Foley catheter 400, can be squeezed through the opening 521 and into the space or tunnel formed by the inner surface of the proximal sleeve 520. Alternatively, the opening 521 may be narrower than the medical tube, as long as the locking adapter 370 (and the retaining adapter 300) is made of a material that is flexible enough to allow the opening 521 to be enlarged by pushing the free opposing surfaces of the proximal sleeve 520 away from each other to allow the medical tube to be squeezed through the opening 521. Once the medical tube is squeezed through the opening 521 the proximal sleeve 520 returns to its original shape.

As illustrated in FIGS. 1 and 2, the locking adapter 370 fits closely within the retaining adapter 300 while still being free to rotate therein. The locking adapter 370 may be inserted into the retaining adapter 300 by sliding it in the distal direction through the opening in the proximal end of the proximal sleeve 320 with the lever 540 oriented in a substantially upward direction. When (or slightly before) the lever 540 comes into contact with the retainer tab 316 on the distal sleeve 310 the locking adapter 370 may be rotated (in a counterclockwise direction in FIGS. 1 and 2) until the lever 540 is aligned with the lateral opening 319 in the distal sleeve 310.

The locking adapter 370 may then be moved in the distal direction until the raised outer rim 570 abuts against the proximally outer surface of the proximal sleeve 320, which prevents the locking adapter 370 from further distal movement. The lever 540 may then be manually pulled or forced distally beyond the first raised section 312 and rotated (clockwise in FIGS. 1 and 2) across the first raised section 312 until the lever 540 flexes back into its original form and resides in the recessed section 318 of the distal sleeve 310. The lever 540 is preferably made of a material flexible enough to slightly bend or flex, in response to a force applied in the distal direction, so that it may pass over the first raised section 312 and then return to its original form.

In this open or unlocked position, a side edge of the lever 540 abuts an inner edge of the first raised section 312, such that the lever 540 is oriented in a substantially upward manner. In this position, the first opening 521 in the locking adapter 370 is substantially or perfectly aligned with the upper opening 321 in the retaining adapter 300, and the second opening 519 in the locking adapter 370 is substantially or perfectly aligned with the lateral opening 319 in the retaining adapter 300. The first opening 521 and the upper opening 321 preferably have substantially the same dimensions, as do the second opening 519 and the lateral opening 319. Accordingly, when the openings are aligned in the unlocked position, a medical tube, such as the Foley catheter 400, may be inserted through both layers of openings for securement within the securement assembly 10.

To insert the Foley catheter 400 into the securement assembly 10 in the unlocked position, a mid-region or other region of the primary tube 405 is inserted through the lateral opening 319 of the retaining adapter 300 and the corresponding second opening 519 of the locking adapter 370 (and through the neighboring lateral gap). The proximal end of the primary tube 405 is inserted through the upper opening 321 in the retaining adapter 300 and the corresponding first opening 521 in the locking adapter 370. In this position, the primary tube 405 passes through, and is reasonably secured within, the distal sleeve 510 and the proximal sleeve 520 of the locking adapter 370.

If the inflation lumen or tube 410 is not already aligned with the lock indicator 317, the inflation tube 410 is rotated (clockwise in FIGS. 1 and 2) until it protrudes through the opening between the proximal sleeves 320 and 520 and distal sleeves 310 and 510 aligned with the lock indicator 317, as shown in FIG. 1. At this point, the Foley catheter 400 is in its working position.

Once the Foley catheter 400 is in the working position, the locking adapter 370 is rotated (clockwise in FIGS. 1 and 2), via the lever 540, around the medical tube until the lever 540 passes over the projection 314 in the recessed section 318 and abuts the second raised section 313 on the distal sleeve 310. As a result, the Foley catheter 400 is held securely within the securement assembly 10 so that it is prevented from pulling out of the securement assembly 10, as described below.

FIGS. 1 and 2 show the securement assembly 10 in the locked position. The projection 314 assists in holding the lever 540 in the locked position. The lever 540 is preferably made of a material flexible enough to slightly bend or flex, in response to a force applied in the distal direction, so that it may pass over the projection 314 and then return to its original form. If included, the wedge 550 on the proximal sleeve 520 of the locking adapter 370 slides underneath the proximal sleeve 320 of the retaining adapter 300 such that an upper surface of the wedge 550 engages in an interference fit with an inner surface of the proximal sleeve 320 to further secure the locking adapter 370 in the locked position.

In the locked position, portions of the distal sleeve 510 and the bridge 560 of the locking adapter 370 block the lateral opening 319 and the neighboring lateral gap in the retaining adapter 300 so the Foley catheter 400 cannot slide laterally out of the securement assembly 10. Similarly, the portion of the proximal sleeve 520 of the locking adapter 370 including the wedge 550 blocks the upper opening 321 in the proximal sleeve 320 of the retaining adapter 370 so the Foley catheter 400 cannot slide out of the upper opening 321. As a result, the Foley catheter 400 (or other medical tube) is securely held within the securement assembly 10 when the securement assembly 10 is in the locked position.

To remove the Foley catheter 400 from the securement assembly 10, the lever 540 is rotated (counterclockwise in FIGS. 1 and 2) until it abuts the first raised section 312 on the distal sleeve 310. In this position, the first and second openings 521 and 519 in the locking adapter 370 are aligned with the upper and lateral openings 321 and 319, respectively, in the proximal sleeve 320. As a result, the Foley catheter 400 may readily be removed from the securement assembly 10 by pulling it out through the aligned openings.

The medical tubing securement assembly 10 may be, packaged as a kit including the base pad 100, the base plate 200 (including the disc 220), the retaining adapter 300, the locking adapter 370, and instructions for use. In one embodiment, a separate disc may also be included in a kit that includes a variable angle medical tubing securement assembly, as described in U.S. Provisional Application Ser. No. 60/718,619. The kit may be contained in a hermetically sealed package that includes written instructions on the package, inside the package, or separate from the package.

The instructions provide a method for using the medical tubing securement assembly 10. First, the medical tubing, such as a Foley catheter, is introduced into the patient's body. A skin preparation solution can then be applied for enhanced adherence and skin protection, after which the base pad 100 is adhered to the patient's skin. The method described above for inserting the medical tubing into the securement assembly 10 is then performed. The retaining adapter 300 may be attached to the disc 220 on the base plate 200 before or after the medical tubing is secured in the securement assembly 10.

Specific details and examples of variable angle assemblies, base plates, discs, and so forth are described in U.S. Provisional Application Ser. No. 60/718,619. While specific embodiments of a securement assembly 10 have been described herein, any securement assembly in which one or more openings in a retaining adapter and a locking adapter are alignable with one another in an unlocked position, and in which one or both of the adapters are rotatable into a locked position wherein one or more of the openings are blocked, is contemplated by the present invention.

Thus, while several embodiments have been shown and described, various changes and substitutions may of course be made, without departing from the spirit and scope of the invention. The invention, therefore, should not be limited, except by any claims and their equivalents.

What is claimed is:

1. A method for securing a medical article to a patient, the medical article including a primary tube and a secondary tube, comprising:
   providing a locking adapter rotatably disposed within a retaining adapter, the locking adapter having a first opening and a second opening, the retaining adapter having an upper opening and a lateral opening;
   inserting a first portion of the primary tube through the lateral opening and the second opening;
   inserting a second portion of the primary tube through the upper opening and the first opening;
   positioning the secondary tube so that the secondary tube extends through the upper opening and the first opening; and
   rotating the locking adapter relative to the retaining adapter to a locked position.

2. The method as in claim 1, wherein the locking adapter defines a channel having a central axis, and wherein at least a portion of the locking adapter is rotated about the central axis when the locking adapter is moved to the locked position.

3. The method as in claim 1, wherein the second portion of the primary tube is inserted through the upper opening and the first opening before the first portion of the primary tube is inserted through the lateral opening and the second opening.

4. The method as in claim 1 further comprising:
   providing a base plate; and
   engaging the retaining adapter with the base plate.

5. The method as in claim 4 wherein engaging the retaining adapter with the base plate comprises sliding the retaining adapter relative to the base plate.

6. The method as in claim 4 further comprising:
   bending the retaining adapter into a bent configuration; and
   disengaging the retaining adapter from the base plate when the retaining adapter is in the bent configuration.

7. The method as in claim 4 further comprising:
   providing a base pad, the base plate being secured relative to the base pad; and
   adhering the base pad to the skin of a patient.

8. The method as in claim 4 further comprising rotating the retaining adapter relative to the base plate.

9. The method as in claim 8 further comprising rotating the locking adapter relative to the base plate, wherein the retaining adapter rotates relative to the base plate about a first axis and the locking adapter rotates relative to the base plate about a second axis, the second axis being different than the first axis.

10. The method as in claim 9 wherein the first axis is not parallel to the second axis.

11. The method of claim 1 further comprising actuating a lever on the locking adapter when rotating the locking adapter relative to the retaining adapter, the lever extending through the retaining adapter at least when the locking adapter is in the locked position.

12. A method for securing a medical article to a patient, the medical article including a first tube and a second tube, the second tube intersecting the first tube, comprising:
   providing a locking adapter secured within a retaining adapter, the locking adapter having a first opening and a second opening, the retaining adapter having a central axis, a third opening, and a fourth opening;
   inserting one of the first and second tubes through the fourth opening and the second opening;
   inserting one of the first and second tubes through the third opening and the first opening;
   positioning one of first and second tubes to extend through the third opening and the first opening; and
   rotating the locking adapter about the central axis of the retaining adapter.

13. The method of claim 12, wherein the first opening is disposed in a first proximal sleeve, and wherein the second opening is disposed in a first distal sleeve, the first proximal sleeve defining at least a portion of the locking adapter and being connect to the first distal sleeve by a bridge.

14. The method of claim 12, wherein the fourth opening is not longitudinally aligned with the third opening.

15. The method of claim 12, wherein the fourth opening is oriented approximately 90° relative to the third opening.

16. The method of claim 12, wherein the third opening is disposed in a first proximal sleeve, and wherein the fourth opening is disposed in a first distal sleeve, the first proximal sleeve defining at least a portion of the retaining adapter and being connect to the first distal sleeve by a bridge.

17. A method for securing a medical tube to a patient, comprising:
   providing a locking adapter rotatable within a retaining adapter;
   inserting a medical tube through aligned openings in the retaining adapter and the locking adapter; and
   rotating the locking adapter relative to the retaining adapter to move the opening in the locking adapter out of alignment with the opening in the retaining adapter.

18. The method of claim 17 further comprising securing the retaining adapter relative to the patient.

19. The method as in claim 17, wherein the locking adapter defines a channel having a central axis, and wherein at least a portion of the locking adapter is rotatable about the central axis.

20. The method as in claim 17 further comprising engaging an elevated wedge on an outer surface of the locking adapter with an inner surface of the retaining adapter when the opening in the locking adapter is out of alignment with the opening in the retaining adapter.

\* \* \* \* \*

UNITED STATES PATENT AND TRADEMARK OFFICE
CERTIFICATE OF CORRECTION

| | | |
|---|---|---|
| PATENT NO. | : 8,679,067 B2 | Page 1 of 1 |
| APPLICATION NO. | : 13/470719 | |
| DATED | : March 25, 2014 | |
| INVENTOR(S) | : Wright | |

It is certified that error appears in the above-identified patent and that said Letters Patent is hereby corrected as shown below:

In the Specification

In column 2 at line 19, Change "into," to --into--.

In column 6 at line 64, Change "48 and 58," to --4B and 5B,--.

In column 9 at line 17, Change "be," to --be--.

Signed and Sealed this
Sixteenth Day of September, 2014

Michelle K. Lee
*Deputy Director of the United States Patent and Trademark Office*